United States Patent [19]

Häubl et al.

[11] Patent Number: 4,990,551
[45] Date of Patent: Feb. 5, 1991

[54] ABSORBING POLYMER

[75] Inventors: Georg Häubl, Linz; Willibald Scheuchenstuhl, St. Oswald, both of Austria

[73] Assignee: Chemie Linz Gesellschaft m.b.H., Linz, Austria

[21] Appl. No.: 427,683

[22] Filed: Oct. 13, 1989

[30] Foreign Application Priority Data

Oct. 14, 1988 [AT] Austria ................... 2559/88

[51] Int. Cl.$^5$ ............... C08L 1/00; C08L 1/26; C08G 63/48
[52] U.S. Cl. .................. 524/30; 524/45; 525/54.21; 525/54.23; 525/56; 525/57
[58] Field of Search ........... 524/45, 30; 525/54.21, 525/54.23, 56, 57

[56] References Cited

U.S. PATENT DOCUMENTS

| | | | |
|---|---|---|---|
| 3,936,441 | 2/1976 | Holst et al. | 536/44 |
| 3,941,730 | 3/1976 | Solenberger | 524/45 |
| 4,169,818 | 10/1979 | DeMartino et al. | 524/43 |
| 4,200,557 | 4/1980 | Chatterjee et al. | 525/54.23 |
| 4,332,917 | 6/1982 | Heslinga et al. | 521/134 |
| 4,338,417 | 7/1982 | Heslinga et al. | 525/197 |
| 4,789,716 | 12/1988 | Scholz et al. | 526/201 |

FOREIGN PATENT DOCUMENTS

| | | |
|---|---|---|
| 0014258 | 8/1980 | European Pat. Off. . |
| 0210754 | 2/1987 | European Pat. Off. . |
| 0272074 | 6/1988 | European Pat. Off. . |
| 2923435 | 12/1980 | Fed. Rep. of Germany . |
| 1392624 | 4/1975 | United Kingdom . |
| 1508123 | 4/1978 | United Kingdom . |
| 2027714 | 2/1980 | United Kingdom . |
| 2046773 | 11/1980 | United Kingdom . |
| 2046774 | 11/1980 | United Kingdom . |

OTHER PUBLICATIONS

Suzuki et al., J. Polym. Sci., 22, 2829–2839 (1984).
CIPAC Handbook, vol. 1, Analysis of Technical and Formulated Pesticides, R. Ashworth et al., 875–879 (1970).

*Primary Examiner*—Morton Foelak
*Assistant Examiner*—P. Hampton-Hightower
*Attorney, Agent, or Firm*—Wenderoth, Lind & Ponack

[57] ABSTRACT

Absorbing polymer consisting of a polymer A which is an optionally modified polyvinyl alcohol or an optionally modified polysaccharide or a mixture of these, and of a polymer B which is a maleic anhydride homo- or copolymer having a hydrolysis time of 5 to 120 minutes, the anhydride groups being open and 0.005 to 5 mol % of the acid functions being esterified with hydroxyl groups of polymer A, and the remaining acid functions being present as free acid groups, as salts or as acid amide groups, an absorbing product containing this polymer and a process for their preparation.

10 Claims, No Drawings

ABSORBING POLYMER

The invention relates to a novel, absorbing polymer and to an absorbing product containing the former, to a process for their preparation and to their use for taking up and retaining water or aqueous solutions.

Absorbing polymers usually consist of polymers or copolymers which are hydrophilic and which have been rendered water-insoluble by reaction with suitable crosslinking agents. Such materials can absorb and hold liquids or steam, so that they are most widely used in a wide range of fields, but in particular in the sanitary sector. In connection with a support, they are employed in all situations where liquids are to be removed rapidly, that is to say, for example, in tissue papers, nappies, tampons, bandages etc. On the other hand, such polymers can also be used with good success for retaining and later releasing moisture in the agricultural sector, but also in many other areas. There has therefore been no lack of attempts to provide such polymers.

For example, in DE-A-2,923,435 there is disclosed a process for the preparation of a crosslinked polyvinyl alcohol (PVAL), in US-A-3,936,441 a process for the preparation of crosslinked cellulose in GB-A-2027714 a process for the preparation of crosslinked carboxyalkyl cellulose and in GB-A-1,508,123 a process for the preparation of crosslinked starch having absorbing properties. Besides the fact that these crosslinked hydrophilic polymers often contain a high proportion of water-soluble products, the crosslinking agents employed are poisonous monomers containing epoxy, halogen or acrylic groups Since the crosslinked, polymeric materials always contain a certain amount of still unreacted, monomeric crosslinking agents, their use in particular in the sanitary sector can cause effects which are injurious to health.

US-A-4,332,917 describes the preparation of a ester in an organic solvent. For this purpose, the maleic anhydride groups are at least partially hydrolized, the two polymers are mixed in an organic solvent, and the solvent is evaporated. In EP-A-0,210,754 there is described a composition of polyalkylene oxides with copolymers which consist of units of an alpha-beta unsaturated monomer and a monomer which is copolymerizable with the former, for the preparation of a water-absorbing composition. However, in both cases the specific polymers are only held together via hydrogen bonds.

From GB-A-1392624 it is known to crosslink polyethylene oxide with water-soluble polymers with the aid of ionizing radiation. However, plants which make possible the irradiation of substrates with ionizing radiation require complicated equipment and extensive protective measures.

Unexpectedly, it was possible with the aid of the present invention to prepare an absorbing polymer which overcomes the disadvantages associated with the abovementioned polymers and their preparation.

Accordingly, the invention relates to an absorbing polymer consisting of a polymer A and a polymer B, comprising polymer A being present in an amount of 10 to 99 percent by weight and being an optionally modified polyvinyl alcohol or an optionally modified polysaccharide or a mixture of these, and polymer B being present in an amount of 1 to 90 percent by weight and being a maleic anhydride homo- or copolymer having a hydrolysis time of 5 to 120 minutes, the anhydride groups being opened and 0.005 to 5 % of the acid functions being esterified with the hydroxyl groups of polymer A and the remaining acid functions being present as free acid groups, as salts or as acid amide groups.

Polymer A is an optionally modified polyvinyl alcohol (PVAL) or an optionally modified polysaccharide or a mixture of such polymers. PVAL is taken to mean conventional polyvinyl alcohols having molecular weights of about 10000 to 100000. Modified PVAL means that some of the hydroxyl groups of the PVAL are present in an esterified or etherified form. Esterified PVAL is understood as meaning either partially hydrolyzed polyvinyl acetate or completely or partially hydrolyzed polyvinyl acetate which is re-esterified. Compounds which are suitable for esterifying PVAL are, for example, reactive derivatives of di- or tricarboxylic acids, such as, for example, acid anhydrides of succinic acid, maleic acid, fumaric acid, itaconic acid or pyromellitic acid. The degree of substitution DS after the esterification is 0.005 to 0.5, preferably 0.01 to 0.3. Such products are commercially available or they can be prepared by a conventional esterification method, for example with the aid of a reactive carboxylic acid derivative, if appropriate in a diluent, using basic or acid catalysts. Compounds which are suitable for etherification are aliphatic or araliphatic sulphonic acids, phosphonic acids, carboxylic acids or their salts, and also quaternary ammonium salts having an aliphatic side chain, and in which this side chain carries a reactive leaving group or epoxy group and can, if appropriate, also be substituted by hydroxyl groups. Examples of such compounds are Na 3-chloro-2-hydroxypropanesulphonate, chloromethylsulphonic acid, Na chloromethylphosphonate, Na monochloroacetate or glycidyltrimethylammonium chloride The degree of substitution DS after etherification is 0.005 to 0.5, preferably 0.01 to 0.3. Such products are commercially available or they can be prepared under conventional etherification conditions, in which process the reactive leaving group of the compound employed for etherification and the hydrogen ion from the hydroxyl group of the PVAL are eliminated, if appropriate in a solvent in the presence of a base, this resulting in the formation of an ether bond. In the event that an epoxy group is present in the place of a reactive leaving group, etherification takes place with basic catalysis, in which case, after the etherification reaction, a hydroxyl group is additionally present in the alpha-position relative to the ether oxygen in the aliphatic side chain of the compound used for etherification. Substances which are used for esterification or etherification are known substances of organic chemistry. Preferred as the polymer A is a modified PVAL, for example a PVAL modified by esterification with succinic anhydride.

Possible examples of polysaccharides are starch, dextran, xanthan, water-soluble cellulose derivatives, such as, for example, cellulose ethers, such as hydroxyalkylcellulose, methylcellulose, carboxylmethylcellulose and hydroxypropylcellulose or sodium alginate, guar and similar substances. Modified polysaccharides are polysaccharides in which some of the hydroxyl groups are esterified or etherified with compounds as have been described above in the case of PVALs. Modified polysaccharides are known and commercially available, or they can be prepared as described above in the case of the modified PVALs. Preferred polysaccharides are carboxymethylcellulose or sodium alginate. However, polymer A can also be a mixture of the polymers described above. Examples of preferred mixtures are partially hydrolyzed PVALs and carboxymethylcellulose, or partially hydrolyzed PVAL and sodium alginate. Polymer A is preferably watersoluble.

Polymer B is a maleic anhydride (MA) homo- or copolymer or a mixture of MA homo- and copolymers or a mixture of various MA copolymers, the hydrolysis time being 5 to 120 minutes, preferably 10 to 60 minutes. Hydrolysis time is taken to mean the time in minutes in which the pH of a stirred dispersion of 0.2 g of polymer B in 76 ml of distilled water and 17.5 ml of 0.1 molar NaOH drops from pH 12.4 to pH 10.0 at 25° C. MA homopolymers are known and can be prepared, for example, following US-A-4789716. Preferably used copolymers are those of MA with alkyl vinyl ether, styrene, 2-methylstyrene, monomethoxypolyethylene glycol vinyl ethers or olefins, such as ethylene, propylene, isobutylene, etc., and similar compounds. Maleic anhydride/methyl vinyl ether (MA/MVE) copolymers are particularly preferred. Copolymers of MA with abovementioned compounds are known, or they can be prepared following conventional methods, for example MA/monomethoxypolyethylene glycol vinyl ether copolymers by the method of Tohru Suzuki et al Journal of Polymer Science Polymer Chemistry Edition, Vol. 22, 1984, 2829 to 2839. Polymer B is preferably water-insoluble.

In the absorbing polymer according to the invention, the acid anhydride groups are present in virtually completely open form and, depending on the nature and amount of the base used, a small, but important proportion of them is present as ester groups, occasionally as a salt and free acid groups, and in some cases also as acid amide groups. The degree of neutralization is the proportion of acid functions in mol %, based on the total number of acid functions present, which is present as a salt. It is about 25 to 80 %.

The proportion of polymer A in the absorbing polymer according to the invention is 10 to 99, preferably between 40 and 95 per cent by weight; the proportion of polymer B is 1 to 90, preferably 25 to 60 per cent by weight.

The absorbing polymer according to the invention has an absorption capacity for distilled water of at least 110 to 800 g/g of the dry absorbing polymer an absorption capacity for a 0 9 percent strength aqueous NaCl solution or for an aqueous CIPAC-D standard solution, that is an aqueous solution having a defined ion content, which is described in Example 1 of the present application, of 10 to 120 g/g of the dry absorbing polymer.

It is capable of absorption over a wide temperature range which embraces the conventional application range of about 0° to 50° C., and it is stable in the presence of those liquids which it is to absorb, which, besides water, can also be, for example, blood, urine, perspiration, secretion of wounds, etc. A particular advantage is the fact that it is non-poisonous.

The invention also relates to a process for the preparation of an absorbing polymer, comprising combining an optionally modified polyvinyl alcohol, an optionally modified polysaccharide or mixtures of these with a maleic anhydride homo- or copolymer having a hydrolysis time of 5 to 120 minutes, and the mixture being treated at a temperature of 20 to 120° C. with 0.5 to 1.6 equivalents, added all at once, of an inorganic or organic base per equivalent of maleic anhydride.

The preparation of the absorbing polymer according to the invention can be continuous or batchwise, and, in a first step, polymer A and polymer B are mixed in a solid, dissolved or dispersed form. Suitable diluents or solvents are organic solvents which are inert under the reaction conditions or water, water being preferred In a preferred procedure, polymer A is dissolved in water and polymer B is added in the form of a powder or dispersed in water. The two polymer systems are combined and if appropriate heated, or the polymer systems A and B are heated before they are combined The reaction mixture is treated with an inorganic or organic base at temperatures of 20° to 120° C., preferably at temperatures of about 50° to 90° C. Inorganic bases which can be employed are, for example, alkali metal hydroxides, alkali metal hydrogen carbonates, alkali metal carbonates, ammonia, ammonium hydrogen carbonate or ammonium carbonate, organic bases which can be employed are, for example, amines, such as methylamine, ethylamine, guanidine carbonate etc. The base is preferably employed in the form of aqueous solutions. It is essential for the process that the base is added all at once, that is to say, rapidly and without interruption.

In general, the solutions or dispersions of polymers A and B are employed as concentrated as possible. When the base is added to the reaction mixture of polymers A and B, virtually all maleic anhydride groups of polymer B are opened, and 0.005 to 5 mol % of the acid functions formed as a result of the reaction form an ester bond with the hydroxyl groups of polymer A. This results in a network of polymers A and B which is bonded via covalent bonds and which has a small but important proportion of covalent ester bonds. The number of the covalent ester bonds in the absorbing polymer was determined photometrically via dinitrophenyl hydrazide, which absorbs at 340 nm. After the reaction, some of the acid functions are in the form of a salt and some in the form of a free acid; if ammonia or amines are used, amide bonds can additionally also be formed.

Polymer A and polymer B are employed in a ratio by weight of 10:90 to 99:1, preferably of about 40:60 to about 95:5. 0.5 to 1.6 equivalents of the base are used per equivalent of maleic anhydride in polymer B, so that after the reaction 25 to 80 % of the acid functions are present as a salt and 0 to 50 % as an amide. The remaining acid functions, which are not present in the form of esters, amides or salts, are present in the form of free acid groups.

The reaction time is very short. The rate at which the reaction proceeds depends on the nature and concentration of the specifically employed starting substances, but in particular on the reaction temperature. At room temperature, the reaction proceeds within minutes, at higher temperatures within seconds.

In the course of the reaction, the viscosity of the reaction mixture increases greatly. Comparison experiments have revealed that this can partly be attributed to "intertwining" of the polymers A and B, as described in US-A-4,169,818, but, as an important feature, also to moderate esterification of polymers A and B. To this end, reaction mixtures according to the invention and comparison reaction mixtures were prepared under identical conditions in each case. The only difference between these reaction mixtures was that, in the comparison case, the anhydride groups of polymer B had already been completely hydrolyzed before the base was added, so that esterification with polymer A was no longer possible When the viscosities are compared, it becomes evident that the viscosity of the reaction mixtures according to the invention is substantially higher than the viscosity of the comparison reaction mixtures. This can only be explained by the presence of ester bonds between polymer A and polymer B.

To obtain a dried, absorbing polymer according to invention, the gel formed in the reaction is applied, for example, to a suitable support surface, such as glass, plastic or steel, dried by customary methods, such as, for example, heating, drying in the air, drying in vacuo or lyophilization, peeled off the support surface and used as a foil, or scraped off and comminuted by pounding or grinding so that the absorbing polymer is then present in the form of a film, powder or flakes and is ready for use.

Depending on the field of application, a range of substances such as softeners, surface-active substances, fillers, pigments, UV-absorbing materials, antioxidants, odour-imparting substances, disinfectants and also chemicals suitable for agriculture can be admixed to the dried absorbing polymer or to a dispersion or solution of the absorbing polymer according to the invention, with the proviso that they do not negatively influence the absorption properties of the absorbing polymer according to the invention.

The absorbing polymer according to the invention can be readily and rapidly prepared, it is virtually water-insoluble, it is non-poisonous, has very good absorption properties, and thus represents an enrichment of the art. Accordingly, the absorbing polymer according to the invention can be used in the form of a powder or individual pieces, in the form of foils, fibres, sheet-like structures and similar shapes, for a range of purposes Foils made of the absorbing polymer according to the invention can be used, for example, to construct moisture barriers in the soil. A powder which consists of the absorbing polymer according to the invention, and which can be mixed for example with soil, glass beads, foamed polymers, calcined clay or comminuted plastic, improves the water retention properties of the soil. It is also possible to incorporate active substances into the absorbing polymer according to the invention in any customary manner, thus guaranteeing long-term effectiveness of these active substances.

Furthermore, the absorbing polymer can be combined with one or more supports to give an absorbing product.

Supports which are possible are, for example, fibrous supports, such as woven or unwoven material, such as, for example, cotton tissue, rayon, wool, dressing gauze, paper or cellulose fluff, for example in the form of lengths, sheets or loose fibres, preferably lengths of paper; glass, ceramics or metal, but also materials such as wood, stone or concrete, are also possible.

The absorbing polymer can be applied to the support on one side or both sides, or incorporated and/or applied between several identical or different supports, so that laminates are present which have two or more layers of the absorbing polymer or it is present in connection with loose fibres, such as, for example, cellulose fibres, asbestos fibres or other material, in which case it can be encased between cover sheets, for example of fabric, fleece fabric or paper. It can be applied to the support continuously or batchwise, that is to say, in the form of, for example, strips, dots, lattices etc., or it can be incorporated between 2 or more supports.

Products which are preferred are, for example, products which are used in the sanitary sector, such as, for example, household and industrial tissues, for example, tissue papers, sanitary towels, tampons, surgical sponges or swabs, facial tissues, bandages, swathes etc.

Such absorbing products can be prepared in various manners. The support can be immersed into a dispersion of the absorbing polymer according to the invention in a conventional manner and dried, the dispersion can be sprayed onto the support or supports, or the absorbing polymer is scattered onto the support in the form of a powder and adhesively bonded with the support by suitable measures, such as, for example, steam and/or pressure treatment. To coat fibres, polymer A, polymer B and—all at once—the base can be incorporated into a suspension of fibres, so that the absorbing product is formed directly in the reaction mixture. Furthermore, it is possible to spray polymer A, polymer B and the base in solution or dispersion onto a continuously moving length of support. In this case, polymer A, polymer B and the base can be sprayed on either individually or together.

In a particularly preferred embodiment, an aqueous solution of polymer A is combined with polymer B which is employed in the form of a powder in aqueous dispersion. This dispersion and the solution of the base, both of which are as concentrated as possible, are propelled through nozzles with the aid of pressurized air or steam and sprayed onto the support. In this case, the base can be mixed with polymer A and polymer B either within the nozzle or outside the nozzle If a length of paper is used as the support, and if the reaction mixture is applied in a highly concentrated form and only in small amounts, it is possible for in particular an over-dried paper to take up the entire moisture.

If the support contains free hydroxyl groups, such as, for example, in the case of cellulose-containing supports, the former can be involved in the crosslinking process so that particularly good bonding to the support takes place when the absorbing layer is formed.

The absorbing products have excellent absorption properties, the bonding between support and polymer being good and durable, and they can be prepared easily, rapidly and with a low input of energy and costs, and therefore represent an enrichment of the art.

EXAMPLE 1

Maleic anhydride/methyl vinyl ether (MA/MVE copolymer)

87.3 g of maleic anhydride and 1.46 g of dilauroyl peroxide were introduced into a 2 l Juchheim pressurized reaction vessel, and the reaction apparatus was then flushed with nitrogen. When the apparatus was free from oxygen, 310 g of methyl vinyl ether which had been dried over solid sodium hydroxide and freshly distilled, were added. The reaction mixture was warmed to 55° C. with stirring and maintained at this temperature for 2 hours under pressure. After the mixture had cooled to 20° C., excess methyl vinyl ether was distilled off, and the reaction product was removed from the vessel. This gave 118 g (84.9 % of theory) of an MA/MVE copolymer having the following properties: loss on drying at 105° C.: 0.92 %, at 60° C. in vacuo: 0.25 %. The particle size distribution, which was measured by sieve analysis, gave the following values:

| Particle size (micrometers) | (%) |
|---|---|
| below 32 | 43.6 |
| 32–44 | 7.6 |
| 44–100 | 13.0 |

-continued

| Particle size (micrometers) | (%) |
| --- | --- |
| 100–200 | 14.0 |
| 200–354 | 14.2 |
| 354–500 | 5.8 |
| 500–710 | 0.6 |
| 710–850 | 0.6 |
| 850–1400 | 0.6 |

Conditions: Alpine air-jet sieve, 0.02 bar vacuum; sieving time: 7 minutes The specific viscosity was determined as follows: 0.5 g of MA/MVE copolymer was dissolved in 50 ml of methyl ethyl ketone and the solution was stirred for 1 to 2 hours at room temperature. The specific viscosity was measured with the aid of a Ubbelohde viscometer and was 3.2.

The hydrolysis rate of the MA groups was determined as follows:

17.5 ml of a 0.1 molar aqueous sodium hydroxide solution and 76 ml of distilled water (having a pH of 12.4) were dispersed with 0.2 g of MA/MVE copolymer in a 250 ml round-bottomed flask equipped with a KPG stirrer (blade diameter: 5 cm) at 250 rpm. The pH drop in the measuring apparatus was determined with the aid of a glass electrode. The hydrolysis time is defined as the period in minutes which is required for the pH to drop from pH 12.4 to pH 10.0. The hydrolysis rate was 30 minutes.

EXAMPLE 2

Polymer A: Polyvinyl alcohol (PVAL), Mowiol 8-88, Hoechst, FRG
Polymer B: Maleic anhydride/methyl vinyl ether (MA/MVE) copolymer of Example I 100 g of 5 % by weight aqueous solution of polymer A were heated to 80° C and treated with 5 g of polymer B in the form of a powder, with stirring 30 ml of a 1 molar aqueous sodium hydroxide solution were then added all at once, which resulted in gel formation in the reaction vessel within one minute. The gel was brushed onto a plastic foil and dried at 100° C. 0.17 mol % of the acid functions of polymer BL were present in the form of esters. The absorption properties of the dried gel were determined in the following manner:

The dried gel was scraped off the plastic foil. About 0.2 g were transferred into a teabag and immersed in an aqueous test solution. The test solutions used were, on the one hand, distilled water, on the other hand a CIPAC-D standard solution which is an aqueous solution having an exactly defined ion content (CIPAC, Handbook, Vol. 1, Analysis of Technical Formulated Pesticides, R. Ashworth, J. Henriet, J. F. Lovett, Cellaboration International Pesticide, Analytical Council, 1970, 875 to 879), and a 0.9 % by weight NaCl solution After 24 hours, the teabag was removed from the test solution, placed on a filter paper base and turned without application of pressure until the escape of liquid had ceased (about 4 minutes). After this, the weight of the swelled sample was determined. The absorption capacity AC of the polymerized substance for a test solution was calculated as follows:

$$AC\ (g/g) = \frac{\text{Weight of the swelled sample} - \text{weight of the dry polymer}}{\text{Weight of the dry polymer}}$$

AC-D is the absorption capacity for distilled water
AC-C is the absorption capacity for a CIPAC-D standard solution
AC-N is the absorption capacity of a 0.9 % by weight sodium chloride solution The gel had the following absorption properties:
AC-D: 434
AC-C: 49
AC-N: 49

The same procedure was also used for determining the absorption capacities of the absorbing polymer in the other examples.

EXAMPLE 3

Polymer A: PVAL, Mowiol 4-88, Hoechst, FRG
Polymer B: MA/MVE copolymer of Example 1

A 27 % by weight aqueous solution of polymer A was introduced in a mixing vessel at a flow of 7.4 g/min together with polymer B in the form of a powder, in an amount of 2 g/min, and the mixture was homogenized. The dispersion which formed was continuously withdrawn in an amount of 9.4 g/min, heated to 80° C., mixed with 4 ml/min of a 17 % by weight aqueous sodium carbonate solution, immediately sprayed onto a paper length of width 23 cm, moving at 12.4 m/min, and dried with hot air. To measure the absorption properties of the absorbing product, batches of 3 to 7 samples in the shape of circles were punched out of the coated length of paper, immersed in test solutions as described in Example 1 and then treated as in Example 1. The absorption capacity of the absorbing product for a test solution was calculated as follows:

$$AC\ (g/g) = \frac{\text{Weight of the swelled sample} - \text{weight of the wet support}}{\text{Weight of the dry sample} - \text{weight of the dry support}}$$

The absorbing product had the following absorption properties:
AC-D 244
AC-C: 41

The same procedure was used for determining the absorption capacity of the absorbing products in the other examples.

EXAMPLE 4

Polymer A: PVAL, Mowiol 4-88, Hoechst, FRG
Polymer B: MA/MVE copolymer of Example 1

100 g of a 24.8 % by weight aqueous solution of polymer A were heated to 80° C. and treated with 24.8 g of polymer B in the form of a powder, with stirring. After this, 39.4 g of a 20 % by weight aqueous sodium carbonate solution were added all at once. After about 30 seconds, the reaction mixture started foaming, this resulting in the formation of a foamed product which was brushed on and dried at 100° C.

|  | Without support | On paper |
| --- | --- | --- |
| AC-D | 214 | 203 |
| AC-C | 30 | 19 |
| AC-N | 34 | — |

EXAMPLE 5

Polymer A: PVAL, Mowiol 4-88, Hoechst, FRG
Polymer B: MA/MVE copolymer of Example 1

The procedure of Example 2 was followed, but at a reaction and drying temperature of 25° C., this giving a dried gel having the following properties:

|      | Without support | On paper |
|------|-----------------|----------|
| AC-D | 142             | 191      |
| AC-C | 31              | 25       |
| AC-N | 38              | —        |

0.084 mol % of the acid functions of polymer B were present in the form of an ester.

EXAMPLE 6

Polymer A: PVAL, Mowiol 8-88, Hoechst, FRG
Polymer B: MA/MVE copolymer of Example 1

50 g of a 10 % by weight solution of polymer A were warmed to 80° C. and treated with 1 g of polymer B, with stirring. After this, 30 ml of a 1 molar aqueous ammonium hydrogen carbonate solution were added all at once, which made the reaction mixture foam, and a foamed product was formed.

|      | Without support | On paper |
|------|-----------------|----------|
| AC-D | 393             | 140      |
| AC-C | 36              | 12       |
| AC-N | 33              | —        |

EXAMPLE 7

As described in Example 6, but using 30 ml of a 0.5 molar, aqueous guanidine carbonate solution as the base, a gel being obtained.

|       | On paper |
|-------|----------|
| AC-C  | 24       |
| AC-N: | 34       |

EXAMPLE 8

Polymer A: Carboxymethylcellulose (CMC), Cekol-DVEP Type, Billerud, Sweden;
Polymer B: MA/MVE copolymer of Example 1

100 g of a 5 % by weight solution of polymer A were heated to 80° C. and treated with 5 g of polymer B, with stirring. A gel was formed within one minute by adding 30 ml of a 1 molar aqueous sodium hydroxide solution all at once.

|      | Without support | On paper |
|------|-----------------|----------|
| AC-D | 55              | 65       |
| AC-C | 64              | —        |

EXAMPLE 9

Polymer A: Sodium alginate, Protanal LF 20/60, AMEA, Austria
Polymer B: MA/MVE copolymer of Example 1

4.5 g of polymer A and 4.5 g of polymer B were run into 145 ml of distilled water, and the mixture was then heated to 70° C. with stirring A gel was formed in the course of 2 minutes by adding 28.8 ml of a 1 molar aqueous sodium hydroxide solution all at once.

|      | Without support | On paper |
|------|-----------------|----------|
| AC-D | 208             | 214      |
| AC-C | 72              | 68       |

EXAMPLE 10

Polymer A: Hydroxypropyl starch, Solamyl 9570, AGENA, Austria
Polymer B: MA/MVE copolymer of Example 1

The procedure of Example 9 was followed, but using 160 ml of distilled water, 12 g of polymer A, 6 g of polymer B and 53.8 ml of a 1 molar aqueous sodium hydroxide solution.

|       | Without support | On paper |
|-------|-----------------|----------|
| AC-D  | 220             | 180      |
| AC-C: | 26              | —        |

EXAMPLE 11

Polymer A: Cold-soluble starch, Sobex 242, Südstärke, FRG
Polymer B: MA/MVE copolymer of Example 1

The procedure of Example 9 was followed, but using 160 ml of water, 6 g of polymer A, 3 g of polymer B and 26.9 ml of a 1 molar, aqueous sodium hydroxide solution.

|      | Without support | On paper |
|------|-----------------|----------|
| AC-D | 227             | 123      |
| AC-C | 20              | —        |

EXAMPLE 12

Polymer A: Phosphate guar, Meyprofilm 500, Meyhall, Switzerland
Polymer B: MS/MVE copolymer of Example 1

The procedure of Example 9 was followed, but using 160 ml of water, 6 g of polymer A, 6 g of polymer B and 38.4 ml of 1 molar aqueous sodium hydroxide solution.

|      | Without support | On paper |
|------|-----------------|----------|
| AC-D | 152             | 215      |
| AC-C | 18              | 28       |
| AC-N | 22              | —        |

EXAMPLE 13

Polymer A: Depolymerized guar, Meyprogat 90, Meyhall, Switzerland
Polymer B; MA/MVE copolymer of Example 1

The procedure of Example 9 was followed, but using 160 ml of water, 3 g of polymer A, 3 g of polymer B and 19.2 ml of a 1 molar aqueous sodium hydroxide solution.

|      | Without support | On paper |
|------|-----------------|----------|
| AC-C | 25              | 14       |
| AC-N | 12              | —        |

EXAMPLE 14

Polymer A: Native guar, Meyproguar CSA 200/50, Meyhall, Switzerland
Polymer B: MA/MVE copolymer of Example 1

The procedure of Example 9 was followed, but using 160 ml of water, 3 g of polymer A, 3 g of polymer B and 26.9 ml of a 1 molar aqueous sodium hydroxide solution.

|  | Without support |
|---|---|
| AC-D | 113 |
| AC-C | 23 |
| AC-N | 22 |

EXAMPLE 15

Polymer A: Hydroxypropyl starch, Solamyl 9570, AGENA, Austria, and PVAL, Mowiol 4-88, Hoechst, FRG, in the ratio of 1:1
Polymer B: MA/MVE copolymer of Example 1

50 g of a 5 % by weight aqueous hydroxypropyl starch solution was made into a paste and treated at room temperature with 12.5 g of a 20 % by weight PVAL solution, and the mixture was heated to 80° C., after which 5 g of polymer B were added with stirring. A gel was formed within one minute after 30 ml of a 1 molar aqueous sodium hydroxide solution were added all at once.

|  | Without support | On paper |
|---|---|---|
| AC-D | 308 | 247 |
| AC-C | 28 | 22 |
| AC-N | 32 | — |

EXAMPLE 16

Polymer A: Cold-soluble starch, Sobex 242, Südstärke, FRG, and PVAL, Mowiol 4-88, Hoechst, FRG, in the ratio by weight of 1:1
Polymer B MA/MVE copolymer of Example 1

50 g of a 5 % by weight aqueous starch solution were mixed with 12.5 g of a 20 % by weight aqueous PVAL solution, and the mixture was heated to 80° C and treated with 5 g of polymer B in the form of a powder. A gel was formed after 30 ml of a 1 molar aqueous potassium hydroxide solution were added all at once.

|  | Without support | On paper |
|---|---|---|
| AC-D | 259 | 138 |
| AC-C | 28 | 15 |
| AC-N | 27 | — |

EXAMPLE 17

Polymer A: Sodium alginate, Protanal LF 20/60, AMEA, Austria, and PVAL, Mowiol 4-88, Hoechst, FRG
Polymer B: MA-MVE copolymer of Example 1

100 ml of a 3 % by weight aqueous sodium alginate solution and 7.5 g of a 20 % by weight aqueous PVAL solution were mixed at room temperature, and the mixture was heated to 80° C. and treated with 4.5 g of polymer B in the form of a powder. A gel was formed after 27 ml of a 1 molar aqueous sodium hydroxide solution were added all at once.

|  | Without support | On paper |
|---|---|---|
| AC-D | 250 | 220 |
| AC-C | 67 | 52 |

EXAMPLE 18

The procedure of Example 17 was followed, the ratio by weight of the starting substances sodium alginate:PVAL:MA/MVE copolymer being 1:1:2.

|  | Without support | On paper |
|---|---|---|
| AC-D | 319 | 277 |
| AC-C | 52 | 50 |

EXAMPLE 19

The procedure of Example 17 was followed, the ratio by weight of the starting substances sodium alginate:PVAL:MA/MVE copolymer being 1:0.5:1.5.

|  | Without support | On paper |
|---|---|---|
| AC-D | 333 | 236 |
| AC-C | 48 | 43 |

EXAMPLE 20

Polymer A: Carboxymethylcellulose (CMC), CEKOL HDEG, Billerud, Sweden, and PVAL, Mowiol 4-88, Hoechst, FRG
Polymer B: MA/MVE copolymer of Example 1

80 g of a 4 % by weight aqueous solution of CMC and 16 g of a 20 % by weight aqueous solution of PVAL were heated to 82° C. and treated with 6.4 g of polymer B in the form of a powder. A gel was formed within 1 minute after 38.4 ml of a 1 molar aqueous sodium hydroxide solution were added all at once

|  | Without support | On paper |
|---|---|---|
| AC-D | 289 | 383 |
| AC-C | 64 | 39 |
| AC-N | 55 | — |

EXAMPLE 21

Polymer A: Hydrolyzed wheat starch, Merigum C, Amylum, Belgium, and PVAL, Mowiol 8-88, Hoechst, FRG
Polymer B: MA/MVE copolymer of Example 1

6 g of wheat starch and 6 g of PVAL were made into a paste or dissolved, respectively, in 123 ml of distilled water at 82° C., after which 6 g of MA/MVE copolymer, dispersed in 20 ml of water, were added with stirring. A gel was formed within 30 to 50 seconds after 39 ml of a 1 molar aqueous sodium hydroxide solution were added all at once.

|  | Without support | On paper |
|---|---|---|
| AC-D | 374 | 188 |
| AC-C | 18 | 16 |

| | Without support | On paper |
|---|---|---|
| AC-N | 18 | — |

EXAMPLE 22

Polymer A: Cationic potato starch, Cationamyl 9852, AGENA, Austria, and xanthan gum, Jungbunzlauer, Austria,
Polymer B: MA/MVE copolymer of Example 1

6 g of potato starch and 3 g of xanthan gum were made into a paste or dissolved, respectively, in 140 ml of distilled water at 80° C., and treated with 3 g of polymer B which had been dispersed in 20 ml of water. A gel was formed within 30 seconds after 27 ml of a 1 molar aqueous sodium hydroxide solution were added all at once.

| | Without support | On paper |
|---|---|---|
| AC-D | 144 | 113 |
| AC-C | 19 | 25 |
| AC-N | 17 | — |

EXAMPLES 23–27

3 g of a range of comminuted cellulose materials were incorporated in 100 g of a 5 % by weight PVAL solution (Mowiol 8-88, Hoechst, FRG), and the mixture was stirred to form fine fibres This mixture was heated to 80° C. and treated with 8 g of MA/MVE copolymer of Example 1. A gel was formed within 20 seconds after 48 ml of a 1 molar aqueous sodium hydroxide solution were added all at once.

EXAMPLE 23

Cellulose material Photocellulose, Borregaard, Austria
PVAL:Cellulose:MA/MVE copolymer = 1:0.6:1.6 (5 g:3 g:8 g) 48 ml of 1 molar NaOH

| | Without support | On paper |
|---|---|---|
| AC-D | 334 | 254 |
| AC-C | 24 | 23 |
| AC-N | 18 | — |

EXAMPLE 24

Cellulose material: Sulphatecellulose, degree of freeness 12° SR, whiteness 88.7 %, Pöls, Austria
PVAL:Cellulose:MA/MVE copolymer = 1:0.6:1.6 (5 g:3 g:8 g)
48 ml of 1 molar NaO

| | Without support | On paper |
|---|---|---|
| AC-D | 390 | 256 |
| AC-C | 25 | 19 |
| AC-N | 18 | — |

EXAMPLE 25

Cellulose material:tissue paper. A, Zewa, PWA FRG
PVAL:Cellulose:MA/MVE copolymer = 1:0.6:1.6 (5 g:3 g:8 g) 48 ml of 1 molar NaOH

| | Without support | On paper |
|---|---|---|
| AC-D | 284 | 251 |
| AC-C | 29 | 27 |
| AC-N | 22 | — |

EXAMPLE 26

Cellulose material: tissue paper B. Henry, Laakirchen, Austria
PVAL:Cellulose:MA/MVE copolymer =1:1:2 (5 g:5 g: 10 g) 60 ml of 1 molar NaOH

| | Without support | On paper |
|---|---|---|
| AC-D | 227 | 196 |
| AC-C | 23 | 28 |
| AC-N | 23 | — |

EXAMPLE 27

Cellulose material, sulphite cellulose, fully bleached Steyrermühl, Austria
PVAL:Cellulose:MA copolymer = 1:1:2 (5 g:5 g:10 g) 60 ml of 1 molar NaOH

| | Without support | On paper |
|---|---|---|
| AC-D | 218 | 204 |
| AC-C | 20 | 18 |
| AC-N | 17 | — |

0.113 mol % of the acid functions of polymer B were present in the form of esters.

EXAMPLE 28

PVAL succinate 100 g of a 36 % by weight aqueous PVAL solution (Mowiol 4-88, Hoechst, FRG) were stirred with 24.5 g of succinic anhydride and 0.3 g of concentrated sulphuric acid for 1 hour at 60° C. The reaction mixture was then cooled to room temperature and added dropwise to acetone, PVAL succinate being precipitated. The precipitate was filtered off, washed with acetone and dried at 50° C. to constant weight This gave 45 g of PVAL succinate. The degree of substitution DS was determined titrimetrically. The degree of substitution was 0.149 mol of succinic ester groups per mol of hydroxyl groups in the PVAL.

PVAL succinates having degrees of substitution of 0.016; 0.038; 0.091 and 0.293 mol of succinic ester groups per mol of hydroxyl groups in the PVAL were prepared following the above procedure using appropriate amounts of succinic anhydride.

Compounds 29 to 33 were prepared following the procedure of Example 2 and using, in each case, 5 g of PVAL succinate of the appropriate degree of substitution DS, 5 g of polymer B and 30 ml of 1 molar aqueous sodium hydroxide solution:

EXAMPLE 29–33

Polymer A: PVAL succinate of degree of substitution DS
Polymer B: MA/MVE copolymer of Example 1

| No. | DS | AC-D without support | AC-C without support | AC-N without support |
|---|---|---|---|---|
| 29 | 0.016 | 431 | 54 | 50 |
| 30 | 0.038 | 398 | 61 | 52 |
| 31 | 0.091 | 353 | 64 | 48 |
| 32 | 0.149 | 400 | 64 | 41 |
| 33 | 0.293 | 424 | 61 | 43 |

EXAMPLE 34

PVAL hydroxypropanesulphonic acid ether 100 g of a 20 % by weight aqueous solution of PVAL, Mowiol 8-88, Hoechst, FRG, were treated with 17.8 g of a 25 % by weight aqueous solution of Na 3-chloro-2-hydroxypropanesulphonate (Na CHPS), and the mixture was heated to 60° C. In this process, the pH was maintained at 8 by dropwise addition of a 20 % by weight aqueous sodium hydroxide solution. When the reaction was complete, the reaction solution was added dropwise to acetone, PVAL hydroxypropanesulphonic acid ether being precipitated. The precipitate was filtered off, washed with acetone and dried. This gave 21 g of PVAL hydroxypropanesulphonic acid ether. PVAL hydroxypropanesulphonic acid ethers were prepared following the above procedure using appropriate amounts of 3-chloro-2-hydroxypropanesulphonic acid ether.

The following polymerized substances were prepared following the procedure described in Example 2 using 120 ml of a 1 molar aqueous sodium hydroxide solution, in each case 20 g of PVAL hydroxypropanesulphonic acid ether as polymer A, dissolved in 80 ml of distilled water, and in each case 20 g of MA/MVE copolymer as polymer B, prepared in Example 1:

EXAMPLES 35-39

| No. | Amount of NaCHPS (25% b.w.) in g | AC-D without support | On paper | AC-C without support | On paper | AC-N without support |
|---|---|---|---|---|---|---|
| 35 | 3.57 | 423 | 347 | 37 | 36 | 34 |
| 36 | 17.84 | 462 | 293 | 47 | 30 | 50 |
| 37 | 39.59 | 326 | 245 | 28 | 20 | 28 |
| 38 | 107.08 | 268 | 398 | 34 | 24 | 43 |
| 39 | 278.48 | 337 | 358 | 34 | 26 | 35 |

EXAMPLE 40

PVAL 2-hydroxypropane-3-(trimethylammonium chloride) ether 0.40 g of glycidyltrimethylammonium chloride were stirred into 200 ml of a 5 % by weight aqueous solution of PVAL, Mowiol 8-88, Hoechst, FRG, of Example 1 at room temperature, and the reaction mixture was heated to 60° C and maintained at pH 8 by continuous addition of an aqueous sodium hydroxide solution. After 2 hours, the reaction mixture was cooled to room temperature, and the product formed was precipitated by adding acetone, filtered off, washed and dried at 50° C. This process gave 10.4 g of the title compound.

EXAMPLE 41

A product having the following properties was obtained following the procedure described in Example 2 and using 5 g of the product of Example 40, dissolved in 100 ml of distilled water, 5 g of MA/MVE copolymer prepared in Example 1 in the form of a powder and 30 ml of a 1 molar aqueous sodium hydroxide solution.

| | Without support |
|---|---|
| AC-D | 373 |
| AC-C | 35 |
| AC-N | 51 |

EXAMPLE 42

6 g of cationic potato starch (Amylofax 15, DS =0.027, AVEBE, NL) and 6 g of PVAL (Mowiol 8-88, Hoechst, FRG) were made into a paste, or dissolved, respectively, in 123 ml of water at 82° C., and the mixture was treated with 6 g of MA/MVE copolymer, prepared in Example 1, and dispersed in 20 ml of water. A gel was formed within seconds after 39 ml of 1 molar aqueous sodium hydroxide solution were added all at once.

| | Without support | On paper |
|---|---|---|
| AC-D | 253 | 159 |
| AC-C | 18 | 16 |
| AC-N | 16 | — |

EXAMPLE 43

6 g of cationic potato starch (Amylofax 15, DS = 0.027, AVEBE, NL) and 3 g of CMC (CEKOL HDEG, Billerud, Sweden), were made into a paste, or dissolved, respectively, in 140 ml of distilled water at 80° C., and the mixture was treated with an aqueous dispersion of 3 g of MA/MVE copolymer, prepared in Example 1, in 20 ml of water. A gel was formed within a few seconds after 27 ml of 1 molar aqueous sodium hydroxide solution were added all at once.

| | Without support | On paper |
|---|---|---|
| AC-D | 230 | 156 |
| AC-C | 32 | 30 |

EXAMPLE 44

Polymer A: Cationic potato starch, Cationamyl 9852, AGENA, Austria

Polymer B MA/isobutyl-ene copolymer, Isobam-10, Kuraray, Japan 6 g of polymer A were made into a paste in 160 ml of distilled water at 70° C., and the mixture was treated with stirring with 3 g of polymer B which had previously been ground in a porcelain dish. A gel was formed after 26.5 ml of a 1 molar aqueous ammonium hydroxide solution were added all at once.

| | Without support |
|---|---|
| AC-D | 127 |

The examples 45 to 48 below prove that the polymerized substance according to the invention is crosslinked via ester bonds and not only via hydrogen bonds.

EXAMPLE 45

1 g of cationic potato starch, Cationamyl 9852, AGENA, Austria, were made into a paste in 150.6 g of distilled water at 70° C. for 20 minutes and the mixture was treated with 0.5 g of MA/MVE copolymer, prepared in Example 1, and dispersed in 9.5 ml of distilled water, and the mixture was stirred for 30 seconds, after which 3.84 ml of a 1 molar aqueous sodium hydroxide solution were added all at once which resulted in the formation of a gel. The solids content of the reaction mixture $$\frac{\text{(solids employed in g} \times 100)}{\text{total weight in g}}$$

was 1 % in this case. After the reaction mixture had cooled to room temperature, the viscosity was determined.

Reaction mixtures of solids contents of 2 % and 3 % were prepared in the same manner using the appropriate amounts of starting substances.

For comparison, reaction mixtures having solids contents of 1, 2 and 3 % were prepared in the same manner but using a MA/MVE copolymer, prepared in Example 1, in which the acid anhydride groups were hydrolyzed completely prior to addition to the reaction mixture by stirring in distilled water for 14 hours, and the viscosities of these reaction mixtures were determined. The degree of neutralization was 60 % in all cases, that is to say, 60 % of the acid groups in the polymerized substance were present in the form of the Na salt, and the pH was 7.5.

The viscosity was determined with the aid of a Brookfield Viscometer, Synchro Lectric Viscometer, Model LVT. The following viscosities were measured:

| Solids content in percent | Viscosity in mPas | |
|---|---|---|
| | According to the invention | Comparison |
| 1 | 520 | 120 |
| 2 | 8350 | 525 |
| 3 | 339000 | 2190 |

EXAMPLE 46

2 g of polyvinyl alcohol, Mowiol 8-88, Hoechst, FRG, were dissolved in 89.1 g of distilled water at 80° C., and the solution was treated with 1 g of MA/MVE copolymer, prepared in Example 1, and dispersed in 9 ml of water, and the mixture was stirred for 30 seconds, after which 3.2 ml of a 1 molar aqueous sodium hydroxide solution were added all at once, which resulted in the formation of a gel. The solids content of the reaction mixture was 3 %. After the reaction mixture had cooled to room temperature, the viscosity was determined.

Reaction mixtures having solids contents of 5 % and 7 % were prepared in the same manner using the appropriate amounts of starting substances, and the viscosities of these reaction mixtures were measured.

For comparison, reaction mixtures were prepared in the same manner, but using a MA/MVE copolymer, prepared in Example 1, in which the acid anhydride groups were completely open prior to the addition to the reaction mixture by stirring in distilled water for 14 hours, and the viscosities of these reaction mixtures were determined. The degree of neutralization was 25 % in all cases and the pH was 4.05.

| Solids content in percent | Viscosity in mPas | |
|---|---|---|
| | According to the invention | Comparison |
| 3 | 1660 | 158 |
| 5 | 7945 | 550 |
| 7 | 36310 | 1740 |

What we claim is:

1. A water absorbing polymer consisting of a polymer a and a polymer b, comprising polymer a being present in an amount of 10 to 99 percent by weight and being a polyvinyl alcohol wherein a part of the hydroxy groups may be esterified or etherified or a polysaccharide wherein a part of the hydroxy groups may be esterified or etherified, or a mixture of these, and polymer B being present in an amount of 1 to 90 percent by weight and being a maleic anhydride homo- or copolymer having a hydrolysis time of 5 to 120 minutes, the anhydride groups being opened and 0.005 to 5% of the acid functions in polymer A and the remaining acid functions being present as free acid groups, as salts or as acid amide groups.

2. The water absorbing polymer according to claim 1, wherein polymer A is a modified polyvinyl alcohol.

3. The water absorbing polymer according to claim 1, wherein polymer A is carboxymethylcellulose.

4. The water absorbing polymer according to claim 1, wherein polymer B is a maleic anhydride/methyl vinyl ether copolymer.

5. The water absorbing polymer according to claim 1, wherein the hydrolysis time of polymer B is 10 to 60 minutes.

6. The water absorbing polymer according to claim 1, wherein polymer A is present in an amount of 40 to 95 percent by weight and polymer B in an amount of 5 to 60 percent by weight.

7. A process for the preparation of a water absorbing polymer comprising combining a polyvinyl alcohol wherein a part of the hydroxy groups may be esterified or etherified, a polysaccharide wherein a part of the hydroxy group may be esterified or etherified or mixtures of these with a maleic anhydride homo- or copolymer having a hydrolysis time of 5 to 120 minutes, and the mixture being treated at a temperature of 20° to 120° C. with 0.5 to 1.6 equivalents, added all at once, of an inorganic or organic base per equivalent of maleic anhydride.

8. The water absorbing product, comprising the absorbing polymer according to claim 1 being bonded to one or more supports.

9. The water absorbing product according to claim 8, comprising the support or supports being one or more lengths of paper.

10. The process for the preparation of an absorbing product according to claim 8, comprising applying a polymer A, a polymer B and an aqueous solution of an inorganic or organic base to and/or between one or more supports, with optional heating, and drying.

* * * * *